United States Patent
Fuhr et al.

(10) Patent No.: US 7,458,285 B2
(45) Date of Patent: Dec. 2, 2008

(54) DEVICE FOR CRYOPRESERVATION OF SAMPLES AND METHOD FOR PRODUCING THE DEVICE

(75) Inventors: Günter Fuhr, Berlin (DE); Heiko Zimmermann, Kronberg im Taunus (DE); Thomas Fixemer, Homburg (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 94 days.

(21) Appl. No.: 10/561,684

(22) PCT Filed: Jun. 23, 2004

(86) PCT No.: PCT/EP2004/006800

§ 371 (c)(1),
(2), (4) Date: Apr. 24, 2006

(87) PCT Pub. No.: WO2005/001439

PCT Pub. Date: Jan. 6, 2005

(65) Prior Publication Data

US 2006/0188865 A1    Aug. 24, 2006

(30) Foreign Application Priority Data

Jun. 26, 2003    (DE) ................. 103 28 869

(51) Int. Cl.
*B01L 11/00* (2006.01)
*G01N 1/42* (2006.01)

(52) U.S. Cl. ............... 73/863.31; 73/864.91; 62/60

(58) Field of Classification Search ........... 73/863, 73/863.31, 864.91, 864, 864.73; 62/62, 60; 435/1.3
See application file for complete search history.

(56) References Cited

U.S. PATENT DOCUMENTS

| | | | | |
|---|---|---|---|---|
| 3,551,951 | A * | 1/1971 | Schiesser | 425/462 |
| 3,993,816 | A * | 11/1976 | Baudet et al. | 428/45 |
| 4,262,494 | A * | 4/1981 | Karow, Jr. | 62/384 |
| 4,388,814 | A | 6/1983 | Schilling | |
| 4,557,903 | A | 12/1985 | McCormick | |
| 4,579,304 | A * | 4/1986 | Williams | 248/68.1 |
| 4,783,973 | A | 11/1988 | Angelier et al. | |
| 5,275,016 | A | 1/1994 | Chatterjee et al. | |
| 5,925,511 | A | 7/1999 | Fuhr et al. | |
| 6,033,880 | A | 3/2000 | Haff et al. | |
| 6,361,934 | B1 * | 3/2002 | Acton et al. | 435/2 |
| 6,646,238 | B1 | 11/2003 | Fuhr et al. | |
| 6,793,893 | B2 * | 9/2004 | Kleinsasser | 422/104 |

(Continued)

FOREIGN PATENT DOCUMENTS

DE    4318089 A1    12/1994

(Continued)

*Primary Examiner*—David A. Rogers
(74) *Attorney, Agent, or Firm*—Caesar, Rivise, Bernstein, Cohen & Pokotilow, Ltd.

(57) ABSTRACT

The invention relates to a sample receiving device (100), particularly for the cryoconservation of at least one sample, including a bundle (10) consisting of a plurality of hose-shaped flexible sample chambers (11, 12, . . .) and a holding device (20) with which the bundle (10) of the sample chambers is joined. The holding device (20) has a plurality of holding frames (21, 22, . . .) which are arranged in a longitudinal direction of the bundle (10).

21 Claims, 3 Drawing Sheets

U.S. PATENT DOCUMENTS

| | | |
|---|---|---|
| 2002/0108957 A1 | 8/2002 | Studer |
| 2003/0035843 A1 | 2/2003 | Livesey et al. |
| 2004/0065093 A1 | 4/2004 | Fuhr et al. |
| 2005/0069861 A1 * | 3/2005 | Zimmermann et al. ....... 435/1.1 |

FOREIGN PATENT DOCUMENTS

| | | | |
|---|---|---|---|
| DE | 19720930 | A1 | 11/1997 |
| DE | 19725768 | A1 | 12/1998 |
| DE | 19826350 | A1 | 12/1999 |
| DE | 19905163 | A1 | 8/2000 |
| DE | 19921236 | A1 | 11/2000 |
| DE | 19922310 | A1 | 11/2000 |
| DE | 10144925 | A1 | 3/2003 |
| DE | 10251668 | A1 | 5/2004 |
| EP | 0475409 | B1 | 4/1998 |
| EP | 0853238 | A1 | 7/1998 |
| EP | 0804073 | B1 | 1/1999 |
| WO | 9602801 | A1 | 2/1996 |

* cited by examiner

DEVICE FOR CRYOPRESERVATION OF SAMPLES AND METHOD FOR PRODUCING THE DEVICE

BACKGROUND OF THE INVENTION

The invention relates to sample receiving devices. The invention also relates to processes for the manufacture and/or the usage of such sample receiving devices.

The cryoconservation is a generally known process for the conservation of particularly biologically (or medically) relevant materials. These materials comprise, for example, cell aggregates, tissue and organs, body liquids or also individual cells or cell constituents, particularly in the dissolved or suspended condition. The cryoconservation is performed according to certain procedures in containers or on substrates wherein the configuration is adapted to the sample with the biological material. Containers used for cryoconservation are known, for example for tissues and organs (refer to DE-OS 199 22 31, EP-A 0 853 238, DE-OS 197 25 768, DE-OS 199 05 163), for blood components (refer e.g. to DE-OS 198 26 350) and for cell or drop type cryosamples (refer e.g. to US-A-5 275 016, EP-B 0 475 409, DE-OS 199 21 236, EP-B 0 804 073).

With the cryoconservation of biological samples, there is a general interest in the quick loading of containers for sample receiving without the involvement of any particular undue effort. Furthermore, it should be possible to manufacture the containers as a mass product in a technologically uncomplicated manner and at a low price. These requirements are fulfilled in particular by hose-type sample chambers which are easy to fill and which can be dismantled, fractionated or otherwise split up in the deep-frozen condition.

For example, it is known from DE 102 51 668 to fix several hose-type sample chambers to a holding frame. The disadvantage with this structural arrangement is that the sample chambers have a very small receiving capacity with practically sensible frame sizes. Furthermore, a disadvantageous aspect can be that an auxiliary unit may be required under certain circumstances for loading the sample chambers. In DE 102 51 668, it is also proposed to use the sample chambers 10' in the form of bundles (refer to FIG. 7). One end of the bundle is secured to a holder 20', on which the sample chambers for example are hung into a cryotank in the suspended condition. Furthermore, a data storage unit for the storage of the sample data is integrated in the holder 20'. Further data storage units can be secured along the length of the bundle.

The conventional hose-type sample chambers have the further disadvantage that a coiling, a meander-shaped placement on a substrate or similar is required for a space-saving and stable location support. Up to the present, this has meant a high assembly work effort with simultaneous restriction of the possibilities for automation.

The object of the invention is to provide improved sample receiving devices (sample containers, cryosubstrates) with which the disadvantages of the conventional sample chambers are overcome and which are characterized in particular by a simplified manufacturing process and/or an improved handling capability with the sample loading, during the freezing operation and during the sample extraction. It is also the object of the invention to provide improved processes for the manufacture and/or for the usage of sample receiving devices, with which the disadvantages related to the manufacture or usage of conventional sample chambers are overcome and which allow in particular an inexpensive and mass-type usage of the cryoconservation.

These objects are solved by sample receiving devices and processes with the features of the patent claims 1 or 18. Advantageous embodiments and applications of the invention result from the dependent claims.

SUMMARY OF THE INVENTION

The invention is based device-related on the general technical teaching to develop further a sample receiving device with a bundle of hollow-line-shaped, particularly hose-type or tubular sample chambers and a holding device with which the bundle of the sample chambers is joined, to the extent that the holding device is established by individual holding frames separated from one another. The inventive formation of a compound made of sample chambers and holding frames attached over their length allows the creation of a ductile and stable belt or train in which the sample chambers have a predetermined arrangement relative to one another. At first the belt forms an endless band from which a sample receiving device, particularly for the cryoconservation of biological materials with the desired dimensions, can be separated, depending in each case on the requirements of a concrete application. The holding frames facilitate furthermore the creation of a compact and low-volume structural arrangement of the sample receiving device without causing any restriction of the receiving capacity of the sample chambers.

The holding frames can each consist of encircling frame parts and serve as holder or carrier of sample chamber sections between the frame parts, between which the sample chambers are arranged in a self-supporting manner. Advantages for the sample extraction can result with this arrangement.

According to the invention, a compound is created from the bundle of sample chambers and the holding frames wherein the holding frames are joined together by means of the sample chambers. The hollow-line-shaped, particularly hose-type or tubular sample chambers form the endless band and, subsequently, a basis or carrier for the holding frames. Advantageously, additional carrier or band materials can be dispensed with.

The bundle of the sample chambers is a collection of similar or different long-stretched hollow chambers consisting of material that is ductile over the length of the bundle. If the sample chambers comprise individual and independent hoses, advantages can result for the manufacture of the sample receiving devices. As an alternative, all sample chambers or groups of sample chambers can be joined at the ends of the bundle, wherein advantages for the loading of the sample receiving device can result.

A holding frame is a carrying or supporting frame-structural component consisting of encircling frame parts that carries the sample chambers. Between the frame parts (for example, rods) of a holding frame, the sample chambers are arranged in a self-supporting manner.

If, according to a preferred embodiment of the invention, the holding frames form plane level carriers on which the sample chambers are arranged next to one another, advantages can result for the observation of the sample chambers and for the access to the samples in frozen condition. The holding frames have preferably a rectangular form in which the sample chambers are aligned in a self-supporting arrangement and in straight orientation.

According to a further preferred embodiment of the invention, the holding frames joined to the bundle of sample chambers can be spaced from one another. This variant can have advantages with regard to the separation of individual holding frames from the train. The distances between the frame parts facing one another are selected in dependence of the concrete requirements. They are preferably larger than 1-times the thickness of the holding frames.

According to an alternative embodiment of the invention, it can be provided that the holding frames are arranged as separate parts, however without distances, along the length of the bundle. The frame parts facing one another have a mutual contact with one another. The holding frames are arranged in flush to one another. This embodiment can have advantages for stock-piling, particularly with the use of sample chambers consisting of rubber-elastic materials. With the formation of a stack by means of mutual flip-over of individual holding frames, there results a deformation and a constriction of the sample chambers between the holding frames. The sample chamber sections in the adjacent holding frames in each case are mechanically separated from each other in this way.

According to a further embodiment of the invention, it can be provided that the distances of the holding frames are selected in such a way that a holding frame can be placed on the adjacent holding frame by a change-around or flip-over without causing damage to the sample chambers between the holding frames.

In a particularly preferable realization of the sample receiving device according to the invention, the holding frames are arranged one above the other so that a compact structural arrangement is advantageously formed. The holding frames form a stack. For the purpose of mutual position fixation, a clamping device such as a clamp or an elastic band can be provided for, with which the holding frames are held together.

According to further variants of the invention, an integrated electronic or optical data storage unit can be provided in each case in at least one or in all of the holding frames so that, in an advantageous manner, the functionality of the sample receiving device can be extended. Additionally or as an alternative, at least one data storage device can be provided along the longitudinal direction of the bundle of the sample chambers between at least two holding frames or at the end of the bundle. In each of the above-mentioned stacks for example, several holding frames and at least one data storage device can be contained.

In general and in accordance with the invention, sample chambers can be used with all forms which are desired for the concrete application. In many cases, the sample chambers along their length have a homogenous form and in particular a constant, for example a round cross-sectional area. Particular advantages of the compound according to the invention consisting of at least two long-stretched sample chambers with a series of holding frames can result if the sample chambers have, with reference to their longitudinal expansion, non-rotation-symmetrical cross-sectional areas and/or a changeable cross-sectional area along their longitudinal expansion. In this case, a pre-specified relative alignment of the sample chambers can be obtained with the holding frames within the bundle and/or over the entire length of the sample chambers.

If the sample chambers according to a first variant have a rectangular cross-section, essentially plane level lateral surfaces of the sample chambers are created, from which there can be advantages for the observation of or measurement on samples. Particularly advantageous is the situation wherein all sample chambers are secured to the holding frames in such a way that, in each case, a plane level lateral surface of the sample chambers is aligned parallel to the plane level expansion of the holding frames.

If the sample chambers according to a further variant have a cross-section that changes along the length of the sample chambers, chamber sections can alternate with a larger and with a smaller cross-sectional area so that compartments or partial chambers are advantageously created. The compartments can facilitate the sample extraction particularly in the frozen condition. Preferably, the cross-section of the sample chambers is periodically changed so that a plurality of compartments is formed.

As an alternative, sample chambers can be provided, which are subdivided by at least one chamber wall into at least two long-stretched partial chambers reaching over the bundle length. Such sample chambers are, for example, multiple compound hoses. The sub-division into partial chambers can be advantageous for special storage techniques for the purpose of, for example, the freezing of samples and reference samples in a solid compound. If the chamber wall is partially permeable according to a further modification, a substance exchange can be realized between the partial chambers, particularly before freezing or after thawing. The partial permeability is achieved preferably by the use of a chamber wall with pores such as in a filter material or a dialysis membrane.

The invention is based process-related on the general technical teaching of providing a sample receiving device according to the invention by means of a simultaneous provision of a plurality of sample chambers, for example by the removal of the sample chambers from delivery rollers or by parallel forming (production e.g. with several extruders), positioning of the holding frames and coiling of the compound from sample chambers and holding frames. This method has the advantage that hollow-line-shaped sample chambers with considerable lengths, e.g. of some meters or some 10 meters, can be joined without the danger of an undesirable looping or coiling to compact sample receiving devices.

If, according to a preferred embodiment of the invention, the holding frames made of plastic are attached to the sample chambers by means of injection molding, the production of the sample receiving device according to the invention can be further simplified in an advantageous manner.

BRIEF DESCRIPTION OF THE DRAWINGS

Advantageous embodiments and applications of the invention are described as follows with reference to the attached drawings. The figures show the following.

DETAILED DESCRIPTION OF PREFERRED EMBODIMENTS

The invention is described as follows with exemplary reference to sample receiving devices with hose sample chambers for the cryoconservation of biological materials. Details of the cryoconservation, particularly with a sample and data storage, are known as such from the state of the art. These details are therefore not described here separately, insofar as they are not of significance for the implementation of the invention.

Figure 1:
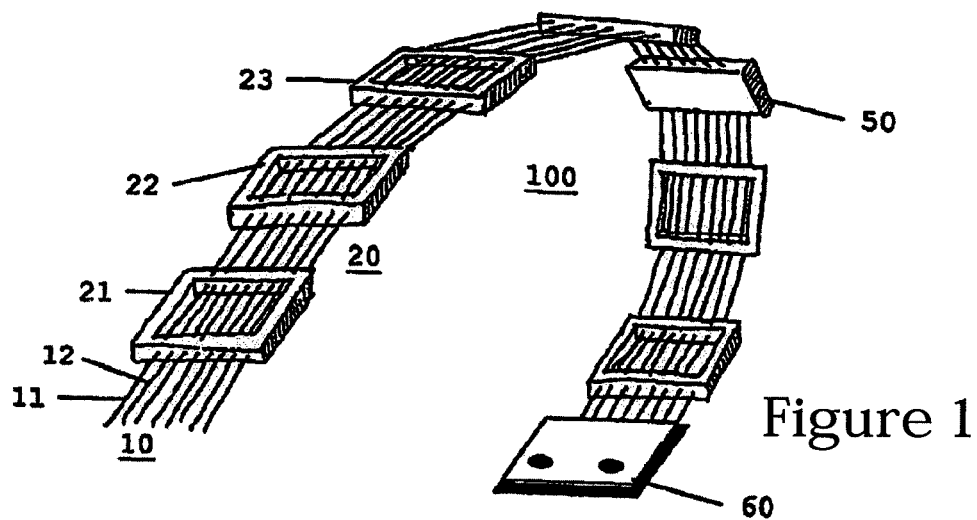
FIG. 1: a schematic illustration of a sample receiving device according to the invention.

The sample receiving device 100 according to the invention comprises according to FIG. 1 the bundle 10 of the sample chambers 11, 12, . . . and the holding device 20. The sample chambers 11, 12, . . . are a plurality of hollow liquid lines which consist of ductile flexible material. The flexibility is established particularly by a plastics material such as, for example, HDPE or PTFE, but with sufficiently small wall thicknesses can also be adequate with metals such as Au, steel or semiconductor materials such as Si or compound materials, in order to realize in particular the roller or stack arrangements described below without causing damage to the sample chambers. The internal diameters of the sample chambers can be in the range of a few µm to for example 15 mm. The wall thickness of the sample chambers can also be varied within this range wherein, as a rule, they are designed so thin that the sample chambers in the frozen (solid) condition can be cut through for sample extraction. The number of the sample chambers is preferably adapted to the formats normally used in biotechnology and lies, for example, in the region between 96 and 256, but can also be selected below (as shown) or above this range.

The holding device 20 comprises the holding frames 21, 22, . . ., which are arranged along the longitudinal extension of the bundle 10 with pre-determined frame distances. The holding frames 21, 22, . . . comprise frame parts with two longitudinal frame parts and two transverse frame parts, which are aligned parallel and transverse to the longitudinal direction of the bundle 10 and which form a rectangle. The holding frames 21, 22, . . . consist of synthetic material, for example PE (in particular HDPE), PTFE, TPX. The sample chambers are formed onto the holding frames by means of injection molding (see below).

The size of the holding frames 21, 22, . . . is selected depending on the application and particularly the number of the sample chambers in each individual case. The length of the longitudinal frame parts can, for example, be selected in the range of 10 mm to 20 cm while the length of the transverse frame parts is designed for the receiving of at least two sample chambers and lies in the range between 5 mm and 20 cm. The thickness of the holding frames is, for example, between about 0.5 to 10 mm. The distances between adjacent holding frames are, for example, in the range of at least 1-times the thickness of the holding frames, particularly 10 mm to 100 mm.

Between two holding frames a data storage device 50 is shown at the sample receiving device 100, showing a data storage unit in a plastic encapsulation with a size that is adapted to the sizes of the holding frames. The configuration and function of the data storage device 50 are known as such so that no further details are given here.

For the purpose of cryoconservation, the sample receiving device 100 can be arranged in a freely suspended manner in a container with an adequately low temperature (for example the temperature of the liquid nitrogen or its vapor). In this case, an end piece 60 can be provided at one end of the bundle 10 for suspension of the sample receiving device 100 in the cryocontainer.

Deviating from the illustrated embodiment of the invention, the holding frames can be provided with different sizes, other geometrical forms (for example other multiple corner forms or round holding frames) or with a changed alignment relative to the bundle longitudinal direction. Furthermore, the bundle 10 can be subdivided into partial bundles, each with smaller holding frames which, partially with common holding frames, are unified to a main bundle. Furthermore, non-plane-level holding frames can be provided.

Figure 2:
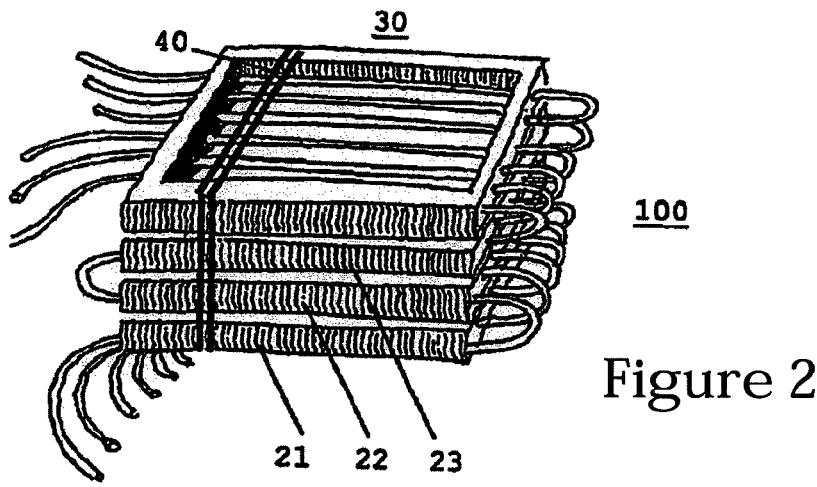
FIG. 2: a sample receiving device according to the invention with a holding frame stack.

FIG. 2 shows the sample receiving device 100 with the arrangement of the holding frames 21, 22, . . . as stack 30. For example, 2 to 10 holding frames, if required with at least one data storage device, are joined to a stack 30. The holding together in the stack 30 is achieved by holding the holding frames together by at least one elastic band 40 or at least one clamp (not shown).

The sample chambers pass through the entire stack 30. For sample loading, the lower ends of the sample chambers can be joined with delivery reservoirs, for example in a micro- or nanotiter plate and the opposing ends with a suction device. In the frozen condition, the loops of the sample chambers formed between the holding frames can be interrupted, through which the sample extraction can be facilitated as required.

Figure 3:
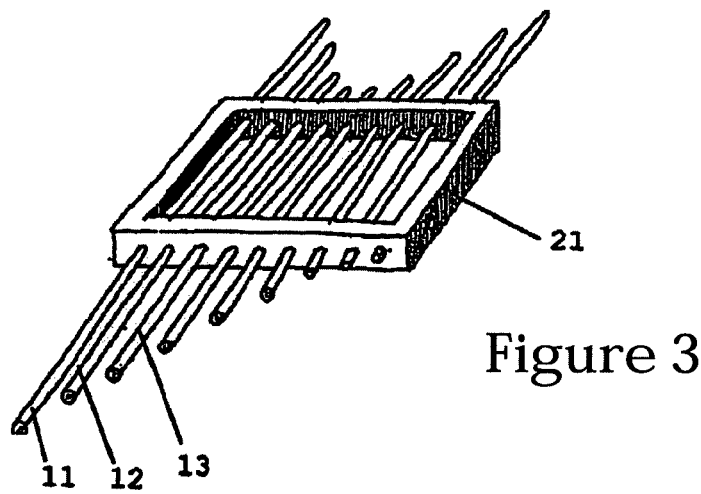
FIG. 3: a partial sample separated from the sample receiving device.

As an alternative, holding frames with lined-up sample chambers, particularly in the frozen condition, can be separated individually from the sample receiving device 100. For example, FIG. 3 shows an individual holding frame 21 with several sample chambers 11, 12 . . . . Outside of the holding frame, the sample chambers 11, 12 . . . protrude with different lengths, a fact which can have advantages for the sample extraction or sample deposition. The ends of the projecting sample chambers form a certain curvature whose shape is determined by a cutting tool for separation of the individual substrate according to FIG. 3 from the sample receiving device 100, and is selected depending on the requirements of a concrete cryoconservation task.

Figure 4:
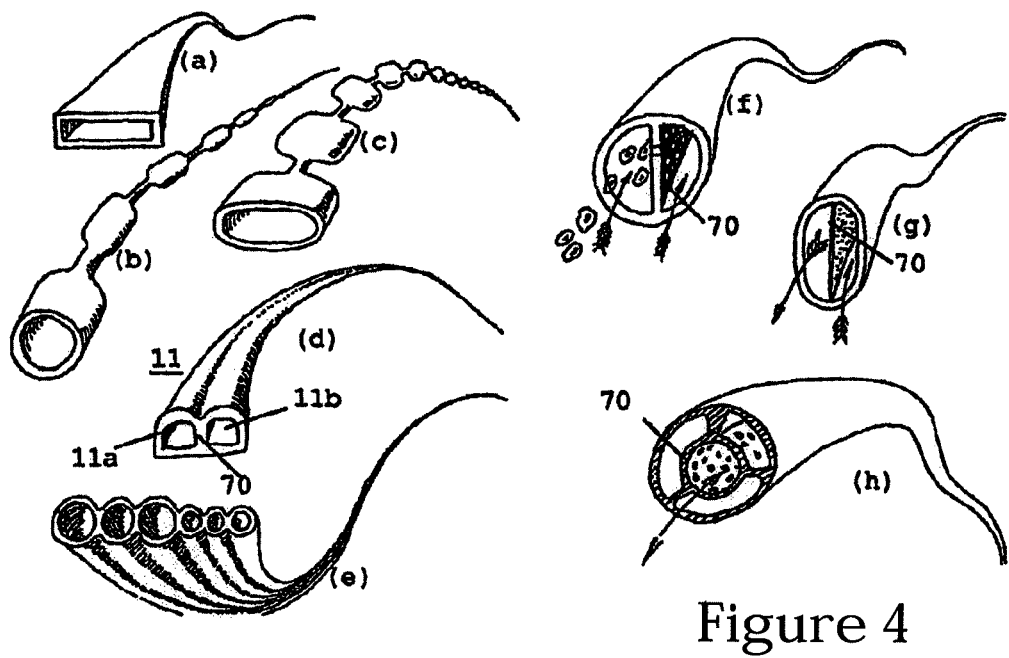
FIG. 4: various forms of sample chambers.
Figure 7:
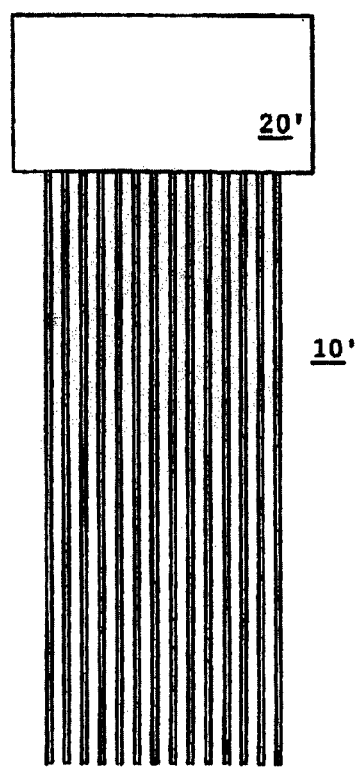
FIG. 7: a conventional sample receiver with hoses (state of the art).

In FIG. 4, sample chambers with non-rotation symmetrical cross-sectional areas or compartments formed in the longitudinal direction, which are used in accordance with the invention are illustrated for the purpose of example. The embodiment of the sample hollow chambers, deviating from the cylinder form, can be significant for special measurement tasks or a microscopic observation of the samples, particularly of cells in the interior of the sample chambers. Particularly sample chambers can be provided with a rectangular cross-sectional area (partial image a) with a round (partial image b) or non-round (partial image c) cross-section area periodically varying in the longitudinal direction, or a compound structure with several partial chambers (partial images d, e) joined in the longitudinal direction. The rectangular chamber of (a) facilitates optical observations at the sample. The compartment formation (creation of lined-up partial chambers which are separated from one another by means of constrictions) serves the purpose of selective extraction of chamber parts in the frozen condition.

The subdivisioning of, for example, the sample chamber 11 (partial image d) into two partial chambers 11a, 11b, which are separated by the chamber wall 70, provides for particular advantages if the chamber wall 70 is semi-permeable so that a substance exchange between the two partial chambers 11a, 11b can be realized. For example, a cell suspension is introduced into the partial chamber 11a, and a nutrient solution with a cryoprotective agent is introduced into the partial chamber 11b. Depending on the time lag between the loading of the partial chambers 11a, 11b up to the freezing process, the amount of cryo-protective agent diffusing into the cell suspension can be set. On the other hand, during the thawing process and by means of a flow of washing solution through the partial chamber 11b, the cryoprotective agent can be withdrawn from the cell suspension in the first partial chamber 11a by means of diffusion. Advantageously in this case, the centrifugation of cells which has been standard practice up to the present is avoided which centrifugation can lead to damage of the thawed-out cells. The band-type combination of sample chambers according to partial image e makes possible that certain cells are accommodated in each partial chamber wherein said cells are to be brought into contact only after thawing (e.g. stem cells with sustentacular cells etc.).

The wall chamber 70 can reach longitudinally through the sample chamber 11 and, in this case, can form a plain partition wall (partial images f, g) or a more complex configuration (partial image a). The chamber wall 70 can be established in a permeable manner with pores (partial image f) or as a dialysis membrane (partial image g) for certain sample constituents. The pores or perforations can have diameters of some micrometers or less, so that the cells cannot pass through the partition wall. If this transition is desired in particular, the pores are then selected in a larger size. The partial images f and g show that, with the sample loading or with the sample treatment after thawing, the flows through the partial chambers with the participating suspensions and solutions can be in the same or in opposing directions. It can be provided according to the invention that the sample chambers as such can be structured from cellulose membranes or from dialysis membranes.

Figures 5, 6:
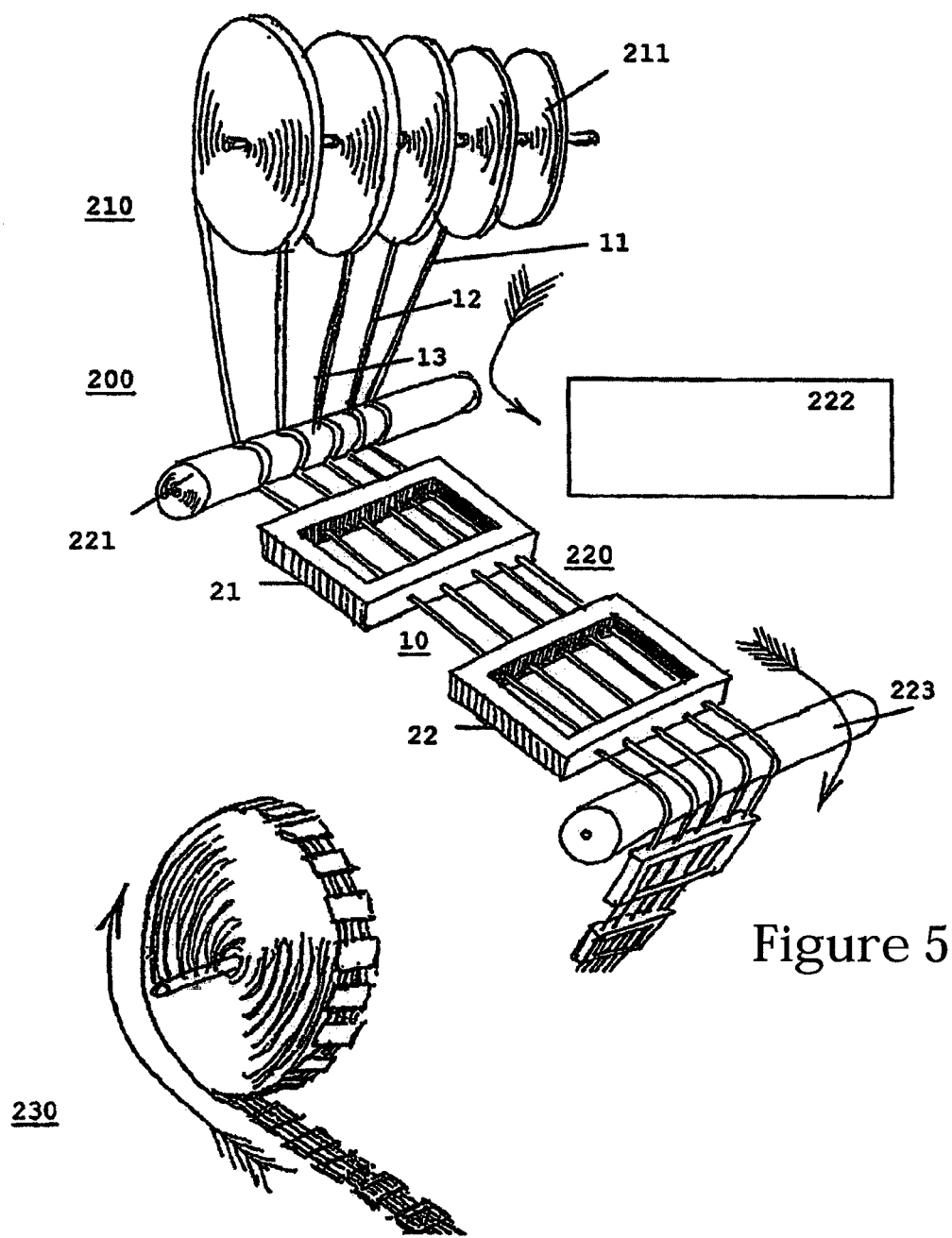
FIGS. 5, 6: illustrations of the manufacture of the sample receiving device according to the invention.

The FIGS. 5 and 6 show the principle of a device 200 for the production of the inventive sample receiving device 100 as an endless cryosubstrate. The device 200 comprises an assembly group 210 for providing the sample chambers, a fixation device 220 for securing the holding frames and a collecting device 230 for accommodating the sample receiving device 100. For the illustrated embodiment, the assembly group 210 comprises delivery rollers 211 on which, in each case, sample chambers are coiled up. The number of the delivery rollers 211 corresponds to the number of the sample chambers to be joined up in the bundle 10. As an alternative, an extruder arrangement can be provided, on which the sample chambers can be produced according to the techniques, known as such, for hose production.

The fixation device 220 comprises a first and a second adjusting device 221, 223 for mutual alignment of the sample chambers in the bundle 10 and a schematically shown jointing device 222 for attaching the holding frames 21, 22, .... In the embodiment shown, the adjusting device 221, 223 comprises two rolls, which if necessary are provided with a structured surface and which specify the distances between the sample chambers on the holding frames.

From the delivery rollers 211, hoses or other hollow band systems, which form the sample chambers, run via the first adjusting device 221 from which the hoses run parallel and freely tensioned by the fixation device 220 up to the second adjusting device 221. By means of the jointing device 222, the sample chambers are jointed into the holding frames 21, 22 with an injection molding process or plastic jointing process, known as such, or the holding frames are formed onto the sample chambers. If the holding frames are formed as clamp frames from two half frames in each case, between which the sample chambers are clamped, a mechanical joining of the half frames at the jointing device can be provided from both sides of the clamped-on sample chambers.

The holding frames fix the sample chambers in the solidly clamped straight form. The fixation for the cryo-conservation is at first non-detachable but can be broken up, for example, for sample extraction with specially adapted tools. Via the second adjusting device 223, the compound of sample chambers and holding frames runs towards the collecting device 230 which comprises, for example, a collecting roller.

The collecting device 230 with the coiled-up sample receiving device 100 represents an embodiment of the invention which can be sent to the user as a finished product. Depending on the concrete requirements, an individual holding frame with the clamped-on sample chambers or a train with several holding frames can then be separated. Sample loading can take place in the rolled-up or separated condition of the sample receiving device.

The features of the invention disclosed in the description as stated in the specification above, in the claims and in the drawings can be of significance both individually as well as in combination for the realization of the invention in its various embodiments.

The invention claimed is:

1. A sample receiving device for cryoconservation of at least one sample, comprising:
    a bundle from a plurality of hose-shaped flexible sample chambers,
    a holding device, with which the bundle of the sample chambers is joined,
    wherein the holding device has a plurality of holding frames with frame parts, between which the sample chambers are positioned in a self-supporting arrangement, where the holding frames are arranged in a longitudinal direction of the bundle; and
    wherein at least one data storage device is provided along the longitudinal direction of the bundle of sample chambers between at least two holding frames or at the end of the bundle.

2. The sample receiving device according to claim 1, wherein the holding frames form plane level carriers, on which the sample chambers are arranged side by side.

3. The sample receiving device according to claim 1, wherein the holding frames establish a rectangular form.

4. The sample receiving device according to claim 1, wherein the holding frames are arranged flush to one another and adjacent in the longitudinal direction of the bundle.

5. The sample receiving device according to claim 1, wherein distances are formed between the holding frames.

6. The sample receiving device according to claim 5, wherein the distances are larger than 1-times a thickness of the holding frames.

7. The sample receiving device according to claim 4, wherein the holding frames form a stack.

8. The sample receiving device according to claim 7, wherein the holding frames are held together in the stack by a clamping device.

9. The sample receiving device according to claim 1, wherein at least one of the holding frames has an integrated data storage unit.

10. The sample receiving device according to claim 9, wherein all holding frames each have an integrated data storage unit.

11. The sample receiving device according to claim 1, wherein the sample chambers have a rectangular cross-section.

12. The sample receiving device according to claim 11, wherein all sample chambers are secured to the holding frames in such a way that, in each case, a plane level lateral surface of the sample chambers is aligned parallel to a plane level expansion of the holding frames.

13. The sample receiving device according to claim 1, wherein the sample chambers have a cross-section which changes along a length of the sample chambers.

14. The sample receiving device according to claim 13, wherein the cross-section of the sample chambers periodically changes.

15. The sample receiving device according to claim 1, wherein the sample chambers are subdivided along their length by at least one chamber wall in at least two partial chambers.

16. The sample receiving device according to claim 15, wherein the chamber wall has pores or is a dialysis membrane.

17. A process for manufacturing a sample receiving device according to claim 1, comprising the steps:
provision or forming of the sample chambers;
forming the bundle of the sample chambers;
attachment of the holding frames in the longitudinal direction of the bundle; and
providing a plurality of holding frames wherein at least one data storage device is provided along the longitudinal direction of the bundle of sample chambers between at least two holding frames or at the end of the bundle.

18. The process according to claim 17, wherein the forming of the sample chambers comprises a parallel extrusion of hoses.

19. The process according to claim 17, wherein the holding frames are attached to the sample chambers by an injection molding process or a clamping process.

20. The process according to claim 17, wherein the provision of the sample chambers comprises an uncoiling of delivery rollers.

21. The process according to claim 20, wherein the forming of the bundle of the sample chambers comprises a simultaneous drawing of the sample chambers from the delivery rollers.

* * * * *